United States Patent [19]

Sas et al.

[11] Patent Number: 6,068,997

[45] Date of Patent: May 30, 2000

[54] METHOD FOR THE CONVERSION OF LECITHIN INTO LYSOLECITHIN

[75] Inventors: Benedikt Sas, Oud-Turnhout; Eric Peys, Balen, both of Belgium

[73] Assignee: Kemin Industries, Inc., Des Moines, Iowa

[21] Appl. No.: 09/259,603

[22] Filed: Mar. 1, 1999

[51] Int. Cl.[7] .............................. C12P 13/00; C12P 7/64
[52] U.S. Cl. .................. 435/128; 435/106; 435/131; 435/134
[58] Field of Search ..................... 435/106, 128, 435/131, 134

[56] References Cited

U.S. PATENT DOCUMENTS

| | | | |
|---|---|---|---|
| 5,153,125 | 10/1992 | Kobayashi | 435/128 |
| 5,213,968 | 5/1993 | Castle et al. | 435/68.1 |
| 5,314,706 | 5/1994 | Colarow et al. | 426/605 |
| 5,650,190 | 7/1997 | Buikstra et al. | 426/602 |
| 5,716,814 | 2/1998 | Yesair | 435/134 |
| 5,759,537 | 6/1998 | Garnett | 424/439 |

FOREIGN PATENT DOCUMENTS

| | | |
|---|---|---|
| 0 398 666 A2 | 11/1990 | European Pat. Off. . |
| 0 531 104 A2 | 3/1993 | European Pat. Off. . |
| 6-2029-950 | 2/1987 | Japan . |
| 2 267 033 | 11/1993 | United Kingdom . |

*Primary Examiner*—Herbert J. Lilling
*Attorney, Agent, or Firm*—Kent A. Herink, Esq.; Daniel A. Rosenberg, Esq.; Davis Brown Law Firm

[57] ABSTRACT

Conversion of crude lecithin is performed by incubating the lecithin with a lipase-phospholipase mixture in a water/polyol environment. The incubation is carried out at about 40–50° C. and a pH of about 7 to about 8 while stirring continuously. The reaction simultaneously produces lysolipid, lysophospholipid, monoglycerides, and diglycerides. The conversion rate of lecithin is more than 80% based on the ratio of LPC/PC (lysophosphatidylcholine/phosphatidylcholine). Calcium chloride can be added to the reaction mixture to capture released fatty acids.

20 Claims, 4 Drawing Sheets

METHOD FOR THE CONVERSION OF LECITHIN INTO LYSOLECITHIN

BACKGROUND OF THE INVENTION

The present invention relates generally to lecithin conversion. More particularly, this invention relates to an improved method of enzymatic conversion of lecithin to produce lysolecithin. Even more particularly, this invention relates to a method of simultaneously producing lysolipid, lysophospholipid, and mono- and diglycerides from lecithin.

Lecithin and lysolecithin have been used in various industries as emulsifiers. These emulsifiers are used in a variety of products, e.g., foods, cosmetics, drugs, nutritional supplements, and chemicals.

Enzymatic conversion of phosphatidylcholine to lysophosphatidylcholine has been known for years. Previous researchers have determined that several factors such as pH, temperature, and surface concentration of the molecules affect this conversion. Additionally, presence or absence of particular ions, such as calcium, or solvents have been determined to affect the conversion process.

These prior art processes have low conversion rates and are unable to produce a cost-effective process.

The process of the current invention converts lecithin at a higher conversion rate while using lecithin, rather than phosphatidylcholine, and producing a desired, product containing lysolipids, lysophospholipids, and mono- and diglycerides.

SUMMARY OF THE INVENTION

Accordingly, it is an object of the present invention provide an improved method for converting lecithin into lysolecithin.

Another object of the invention is to provide a method which simultaneously converts lipids and phospholipids of crude lecithin into lysolipids, lysophospholipids, and mono- and diglycerides.

Another object of the invention is to provide a method which simultaneously converts lipids and phospholipids of crude lecithin into lysolipids, lysophospholipids, and mono- and diglycerides at a greater conversion percentage than prior art methods.

The invention is a method for the improved conversion of lipids and phospholipids present in crude lecithin into their lyso- forms and the simultaneous production of mono- and diglycerides to get an improved emulsifier. This conversion is performed by means of an enzymatic treatment. The enzymatic treatment consists of the hydrolysis and/or alcoholysis of lipids and phospholipids in a water/polyol mixture, by means of a blend of lipase and phospholipase A2. The lipase cleaves ester bonds of the lipids and produces glycerol and mono- and diglycerides. The phospholipase A2 cleaves the ester bond of the phospholipids at the C2 position of the glycerol backbone. The resultant lysophospholipids are surface-active amphiphiles that contain only one long chain fatty acyl group and a large polar head group consisting of a free hydroxyl on the glycerol backbone and an anionic or zwitterionic moiety bonded to the same backbone via a phosphate ester. Common moieties include choline, ethanolamine, and inositol.

The conversion is performed by incubating lecithin with the lipase-phospholipase mixture in an aqueous/polyol environment with or without the addition of calcium chloride ($CaCl_2$) to capture the released fatty acids. The lecithin is mixed with water and polyols at 40–50° C. that has been made slightly basic. This mixture is kept at 50° C. and is continuously stirred. The pH of this mixture is continuously monitored and kept at pH 7 to 8 by addition of a base. When the lecithin and solvent are well-mixed the lipase-phospholipase is added. The conversion is checked by means of an HPLC method of analysis.

Until now the conversion of phospholipids of crude lecithin into lysophospholipids with phospholipase A2 on a large scale resulted in a low conversion percentage. The present method is able to increase the conversion percentage while simultaneously producing mono- and diglycerides. The conversion is more than 80% based on the ratio of LPC/(LPC+PC) (LPC=lysophosphatidylcholine; PC=phosphatidylholine).

DETAILED DESCRIPTION OF THE INVENTION

Figure 1:
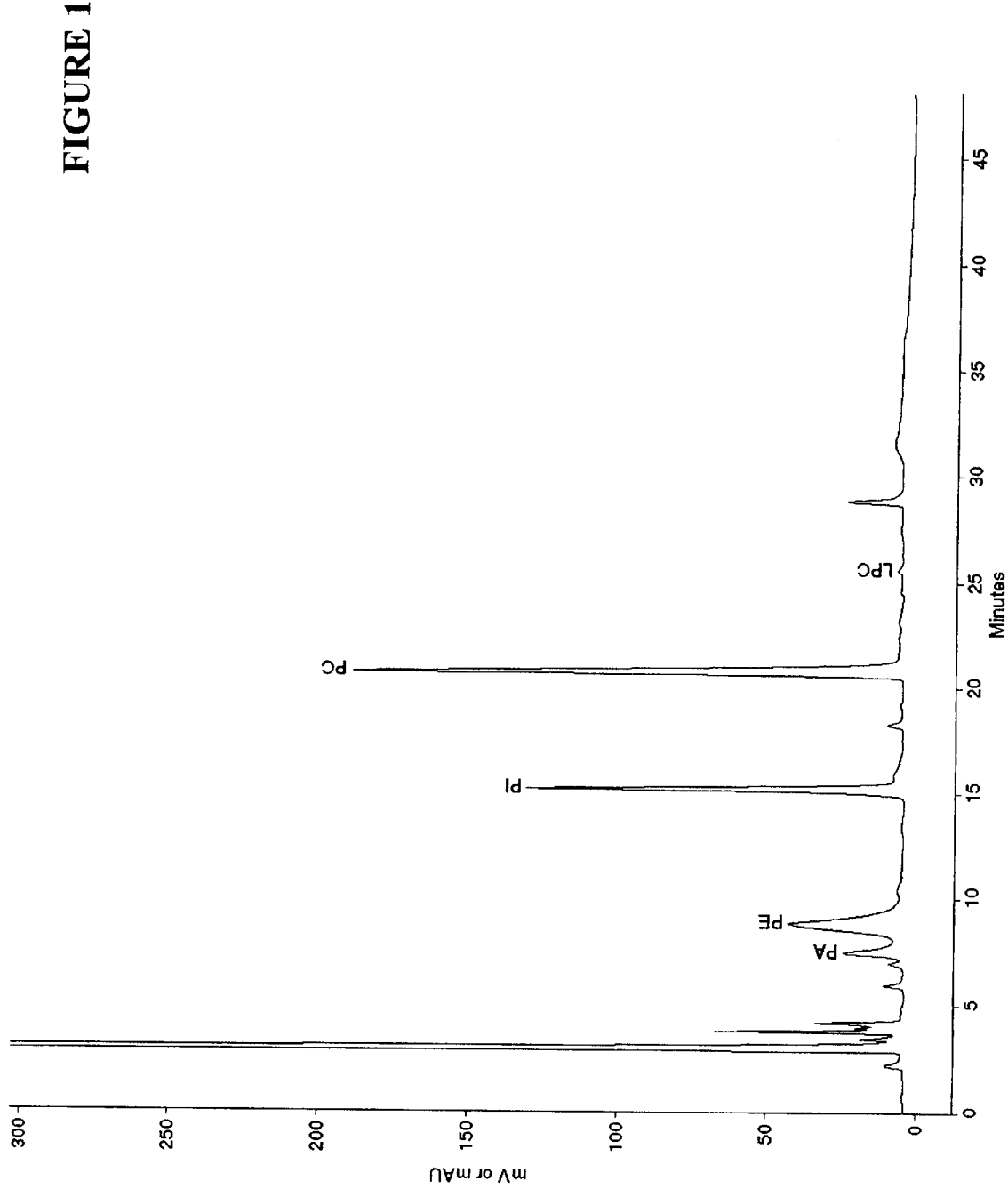
FIG. 1 is a high-performance liquid chromatography-evaporative light-scattering detector (HPLC-ELSD) chromatogram of crude lecithin.

The invention is an improved method for simultaneously producing lysolipids, lysophospholipids, and mono- and diglycerides from crude lecithin. The method produces a high conversion rate of over 80% based on the ratio of LPC/PC (lysophosphatidylcholine/phosphatidylcholine) in a single step.

Crude lecithin can be used in the process of the current invention. Prior art processes generally use phosphatidylcholine. Lecithin is available from various commercial sources.

The lecithin is added to a water/polyol mixture. The water/polyol is in a 6 to 1 weight ratio. The lecithin is added to the mixture in a 3 to 7 weight ratio. In a preferred embodiment of the invention, the water/polyol mixture is at about 40° C. to about 50° C. and has been made slightly basic. The preferred polyol for the process is glycerol. Though this is the preferred polyol, any polyol may be used. The pH of the mixture is preferred to be about 7 to 8. The range of pH that will work depends on the workable pH range of both lipase and phospholipase A2. The pH may be adjusted using a base. A base that has been used is sodium hydroxide (NaOH) at 10N. Any base may be used as long as it does not interfere with the desired reactions. It is desired to keep the combination of lecithin/water/polyol at a constant pH. A pH-stat has been used to achieve a constant pH. The combination of lecithin/water/polyol is preferably continuously stirred.

A blend of lipase and phospholipase A2 is added to the lecithin/water/polyol combination. The lipase and phospholipase A2 enzymes are available from various commercial sources. A lipase/phospholipase A2 mixture from Lovesgrove Research Ltd. has been used. The conversion can be performed with any other combination of lipase and phospholipase A2 as long as there is an overlap in their workable pH range. The activities of the enzymes used in the examples was about 16 units per gram of crude lecithin for the lipase and about 48 units per gram of crude lecithin for the phospholipase A2. One lipase unit is equal to the amount of enzyme that liberates one micromole of fatty acids per minute from tricaprylin under the conditions of the assay (pH=7.5, 40° C.). One phospholipase unit is equal to the amount of enzyme that liberates one micromole of fatty acids per minute from soy phosphatidylcholine under the conditions of the assay (pH=7.5, 40° C.). Though the full range of amounts and ratios of these enzymes that will be effective have not been tested, half the amount of enzymes was effective, albeit over a longer incubation period. This is incubated for a length of time necessary to achieve a desired conversion rate. This length of time is dependent upon the amount and activity of the enzymes added. The end point can be found by checking with HPLC, or by watching the pH-stat data for leveling. The pH-stat data of the preferred embodiment showed conversion completed after approximately 12 hours.

Certain enzymes may required calcium ($Ca^{2+}$) ions to exert their activity. Calcium chloride ($CaCl_2$) can be added to the mixture, though it is not necessary. Calcium chloride is available from various commercial sources. Calcium ions catch the fatty acids that are released during the conversion. Any compound which serves this function but does not interfere with the desired results may be used. The calcium chloride can be added at an amount in moles from zero up to half the number of moles of fatty acids expected to be released during incubation.

The methods of this invention are further illustrated by the following experimental examples.

EXAMPLES

Example 1

Four hundred twenty grams (420 g) of water and 70 g glycerol were mixed. The pH of the mixture was adjusted to 7.5 with NaOH 10N. This mixture was stirred at approximately 100 rpm and kept at a temperature of 50° C. The pH was kept constant at 7.5 with NaOH 10N. A lipase-phospholipase A2 enzyme mixture was added. Two hundred ten grams (210 g) crude lecithin was added, and the mixture was incubated for 18 hours.

Results: Table 1 shows the results of Examples 1–3. There was 3.3% LPC of (LPC+PC) in the crude lecithin. The resulting product of this procedure contained 93.4% LPC of (LPC+PC). See FIGS. 1 and 2 for the chromatograms of the starting and ending materials.

FIG. 1. HPLC-ELSD Chromatogram of starting material (crude lecithin).

Figure 2:
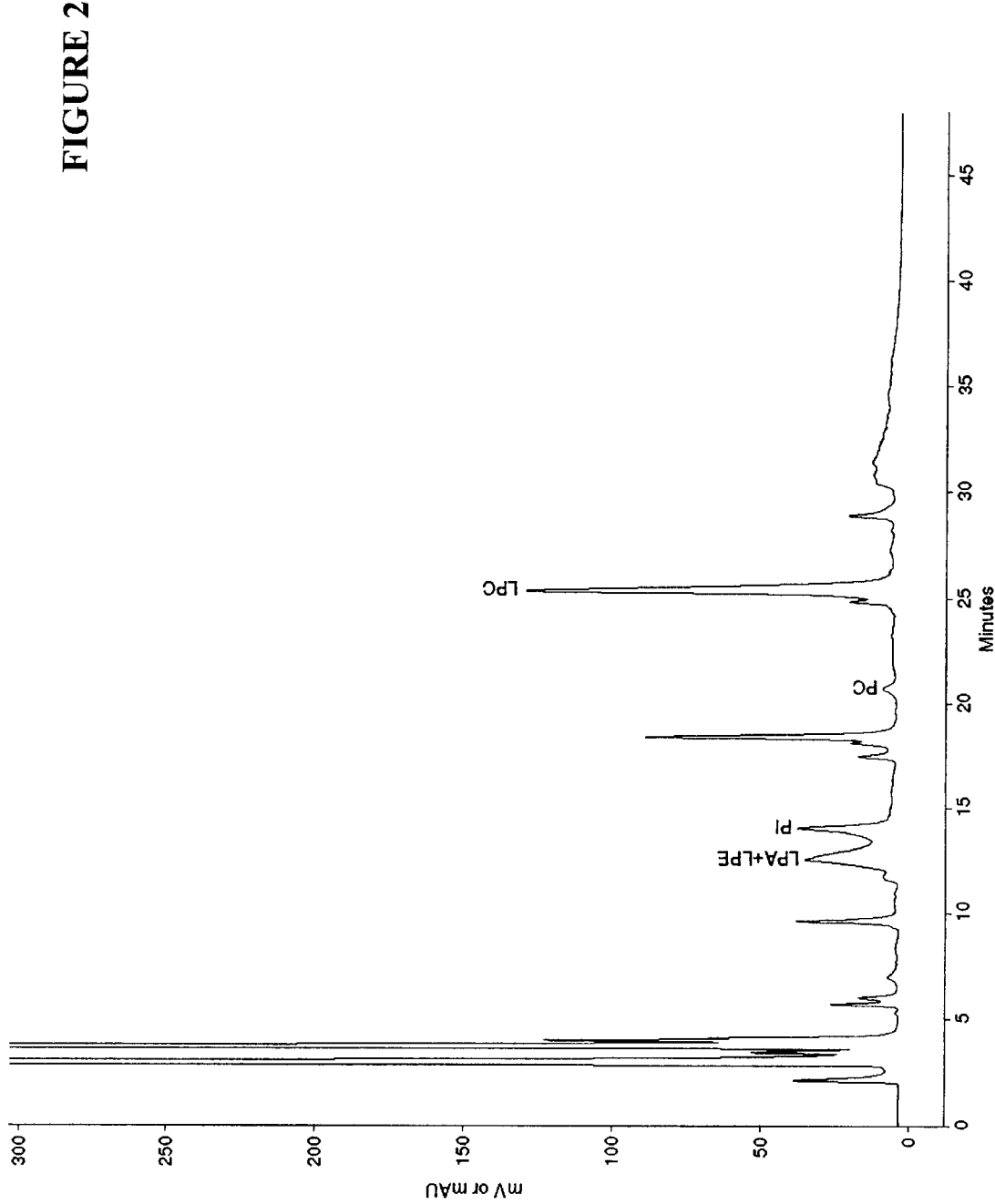
FIG. 2 is a HPLC-ELSD chromatogram of the product of Example 1.

FIG. 2. HPLC-ELSD Chromatogram of the final product using the above procedure of Example 1.

Example 2

Three thousand grams (3000 g) water and 500 g glycerol were mixed. The pH of the mixture was adjusted to 7.5 using NaOH 10N. This mixture was stirred at approximately 100 rpm and kept at 50° C. The pH was constantly kept at 7.5 using NaOH 10N. A lipase-phospholipase A2 mixture was added. Fifteen hundred grams (1500 g) crude lecithin was added, and the mixture was incubated for 21 hours.

Results: Table 1 shows the results of Examples 1–3. The crude lecithin starting material was the same as that of Example 1, i.e., containing 3.3% LPC of (LPC+PC). The resulting product of this procedure contained 95.6% LPC of (LPC+PC). See FIGS. 1 and 3 for the chromatograms of the starting and ending materials.

Figure 3:
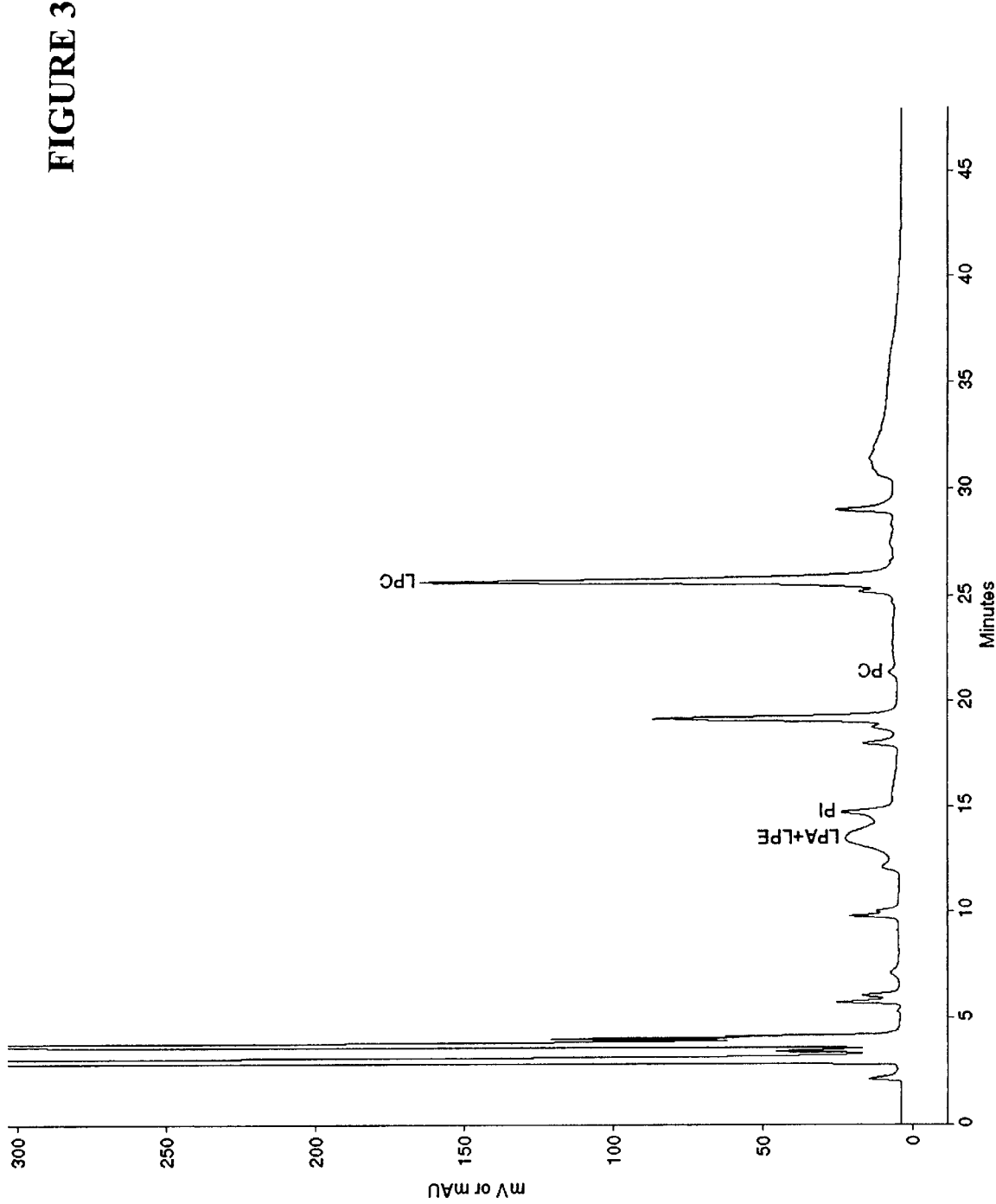
FIG. 3 is a HPLC-ELSD chromatogram of the product of Example 2.

FIG. 3. HPLC-ELSD Chromatogram of the final product using the above procedure of Example 2.

Example 3

Two thousand two hundred twenty grams (2220 g) water and 370 g glycerol were mixed, and the pH of the mixture was adjusted to 7.5 with NaOH 10N. This mixture was stirred at approximately 100 rpm and kept at 50° C. The pH was kept constant using NaOH 10N. A lipase-phospholipase A2 enzyme mixture was added. One thousand one hundred ten grams (1110 g) crude lecithin was added, and the mixture was incubated for 21 hours.

Results: Table 1 shows the results of Examples 1–3. The crude lecithin starting material was the same as that of Example 1, i.e., containing 3.3% LPC of (LPC+PC). The resulting product of this procedure contained 94.4% LPC of (LPC+PC). See FIGS. 1 and 4 for the chromatograms of the starting and ending materials.

Figure 4:
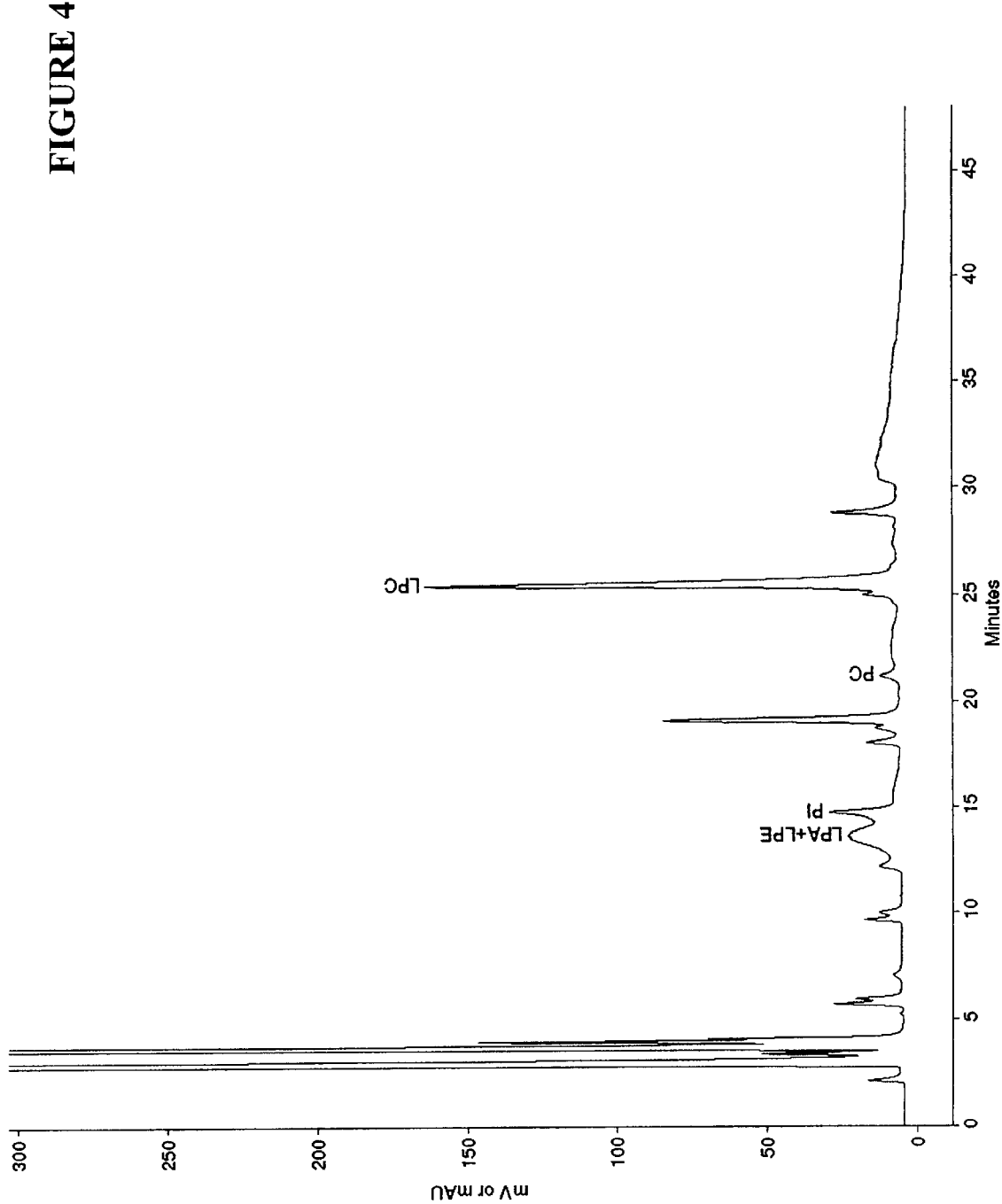
FIG. 4 is a HPLC-ELSD chromatogram of the product of Example 3.

FIG. 4. HPLC-ELSD Chromatogram of the final product using the above procedure of Example 3.

TABLE 1

| Material | % LPC of (LPC + PC) |
| --- | --- |
| Crude Lecithin | 3.3 |
| Lovesgrove | 18 |
| Example 1 Product | 93.4 |
| Example 2 Product | 95.6 |
| Example 3 Product | 94.4 |

Example 4

A competitor's modified lecithin was compared against lecithin converted by the process of the current invention using both P-NMR and the HPLC-ELSD methods. The results are given in Table 2. The Lovesgrove modified lecithin is made via a bacterial/enzymatic conversion using phospholipase A2 (see UK and PCT patent No. 9205014.5 and U.S. Pat. No. 5,759,537).

TABLE 2

| Wt. % | Crude Lecithin | Lovesgrove Research Limited modified lecithin ($^{31}$P-NMR data) | Lovesgrove Research Limited modified lecithin (HPLC data) | Converted Lecithin of Examples 1–3 (HPLC data) |
| --- | --- | --- | --- | --- |
| PA (phosphatidic acid) | 3.21 | 4.82 | 3.01 | |
| PE (phosphatidylethanolamine) | 7.51 | 10.08 | 8.19 | |
| PI (phosphatidylinositol) | 6.87 | 7.93 | 6.88 | 1.4 ± 0.4 |

TABLE 2-continued

| Wt. % | Crude Lecithin | Lovesgrove Research Limited modified lecithin ($^{31}$P-NMR data) | Lovesgrove Research Limited modified lecithin (HPLC data) | Converted Lecithin of Examples 1–3 (HPLC data) |
|---|---|---|---|---|
| LPA + LPE (lysophosphatidic acid and lysophosphatidylethanolamine) | | 1.77 | 1.90 | 5.3 ± 0.7 |
| PC (phosphatidylcholine) | 12.24 | 12.32 | 11.09 | 0.43 ± 0.10 |
| LPC (lysophosphatidylcholine) | 0.42 | 1.99 (1-LPC + 2-LPC) | 1.19 | 7.27 + 0.23 |
| % LPC of (LPC + PC) | 3.3 | 13.91 | 9.69 | 93.4 – 95.6% |

Although the invention has been described with respect to a preferred embodiment thereof, it is to be also understood that it is not to be so limited since changes and modifications can be made therein which are within the full intended scope of this invention as defined by the appended claims.

What is claimed is:

1. A method for simultaneously producing lysolipids, lysophospholipids, monoglycerides, and diglycerides comprising:
    a. combining lecithin with a water/polyol mixture to form a combination,
    b. contacting the combination with a blend of lipase and phospholipase A2,
    c. incubating for a length of time effective to achieve the desired conversion rate.

2. The method of claim 1 further comprising adding calcium chloride to the lecithin/water/polyol combination.

3. The method of claim 2 wherein the calcium chloride is added in a range of about zero moles to about half the number of moles of fatty acids expected to be released during incubation.

4. The method of claim 1 wherein the weight ratio of water to polyol is about 6 to about 1.

5. The method of claim 1 wherein the water/polyol mixture pH is slightly basic.

6. The method of claim 5 wherein the pH is about 7 to about 8.

7. The method of claim 6 wherein the pH is about 7.5.

8. The method of claim 1 wherein the water/polyol mixture is maintained at a temperature of about 40° C. to about 50° C.

9. The method of claim 1 wherein the weight ratio of lecithin to water/polyol is about 3 to about 7.

10. The method of claim 1 wherein the combination of lecithin/water/polyol is continuously stirred.

11. The method of claim 1 wherein the combination of lecithin/water/polyol is kept at a pH of about 7 to about 8.

12. The method of claim 11 wherein the pH is about 7.5.

13. The method of claim 1 wherein the polyol is glycerol.

14. A method for simultaneously producing lysolipid and lysophospholipid and mono- and diglycerides comprising:
    a. combining lecithin with a slightly basic water/polyol mixture at a temperature of about 40° C. to about 50° C. to form a combination,
    b. maintaining the combination at about 40° C. to about 50° C.,
    c. stirring the combination continuously,
    d. maintaining the pH of the combination at about 7 to about 8 using a base,
    e. adding a lipase-phospholipase A2 blend to the well-mixed combination,
    f. incubating for a length of time effective to achieve the desired conversion rate.

15. The method of claim 14 wherein the temperature is about 50° C.

16. The method of claim 14 wherein the pH is about 7.5.

17. The method of claim 14 wherein the base is sodium hydroxide.

18. The method of claim 14 further comprising adding calcium chloride to the lecithin/water/polyol combination.

19. A method for simultaneously producing lysolipid and lysophospholipid and mono- and diglycerides comprising:
    a. combining lecithin with a water/glycerol to form a combination,
    b. adjusting the pH of the combination to about 7.5 using sodium hydroxide,
    c. stirring the combination continuously at approximately 100 rpm and at a temperature of about 50° C.,
    d. maintaining the combination at about 50° C.,
    e. maintaining the pH of the combination at about 7.5 using a sodium hydroxide,
    f. adding a lipase-phospholipase A2 blend to the well-mixed combination,
    g. incubating for approximately 12 hours.

20. The method of claim 19 further comprising adding calcium chloride to the lecithin/water/glycerol combination.

* * * * *

UNITED STATES PATENT AND TRADEMARK OFFICE
CERTIFICATE OF CORRECTION

PATENT NO : 6,068,997
DATED : May 30, 2000
INVENTOR(S): Sas, Benedikt; Peys, Eric It is certified that error appears in the above-identified patent and that said Letters Patent are hereby corrected as shown below:

Column 3, line 4: "phospholipasc" should read --phospholipase--

Signed and Sealed this

First Day of May, 2001

NICHOLAS P. GODICI

*Attest:*

*Attesting Officer*    *Acting Director of the United States Patent and Trademark Office*